United States Patent [19]

Smith

[11] 4,134,921

[45] Jan. 16, 1979

[54] 2-DECARBOXY-2-HYDROXYMETHYL-3,7-INTER-m-PHENYLENE-13,14-DIDEHYDRO-PG COMPOUNDS

[75] Inventor: Herman W. Smith, Kalamazoo, Mich.

[73] Assignee: The Upjohn Company, Kalamazoo, Mich.

[21] Appl. No.: 814,500

[22] Filed: Jul. 11, 1977

Related U.S. Application Data

[62] Division of Ser. No. 708,752, Jul. 26, 1976, Pat. No. 4,058,564.

[51] Int. Cl.$^2$ ............................................. C07C 49/76
[52] U.S. Cl. .................................................. 260/590 C
[58] Field of Search ........................ 260/590 C, 514 D

[56] References Cited

U.S. PATENT DOCUMENTS

| | | | |
|---|---|---|---|
| 3,932,496 | 1/1976 | Jung | 260/514 D |
| 3,935,254 | 1/1976 | Galdolfe et al. | 260/514 D |
| 3,984,400 | 10/1976 | Eggler et al. | 260/468 D |

Primary Examiner—James O. Thomas, Jr.
Assistant Examiner—James H. Reamer
Attorney, Agent, or Firm—Robert A. Armitage

[57] ABSTRACT

This invention comprises certain analogs of the prostaglandins in which the C-1 carboxyl is replaced by a primary alcohol and the double bond between C-13 and C-14 is replaced by a triple bond. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

65 Claims, No Drawings

2-DECARBOXY-2-HYDROXYMETHYL-3,7-INTER-M-PHENYLENE-13,14-DIDEHYDRO-PG COMPOUNDS

The present application is a divisional application of Ser. No. 708,752, filed July 26, 1976, now issued as U.S. Pat. No. 4,058,564 on Nov. 15, 1977.

The present invention relates to prostaglandin analogs for which the essential material constituting a disclosure therefor is incorporated by reference here from U.S. Pat. No. 4,058,564, issued Nov. 15, 1977.

I claim:

1. A prostaglandin analog of the formula

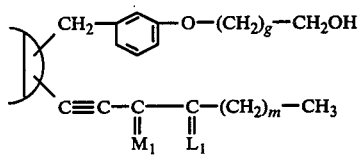

wherein ⟩ is

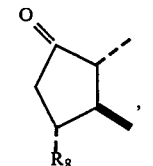

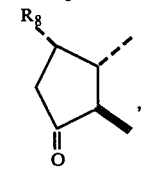

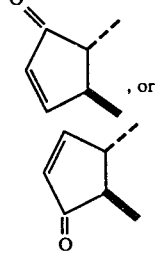

wherein $R_8$ is hydrogen or hydroxy; wherein $M_1$ is

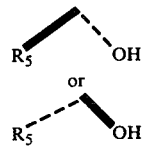

wherein $R_5$ is hydrogen or methyl; wherein $L_1$ is

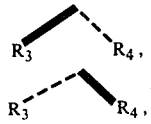

or a mixture of

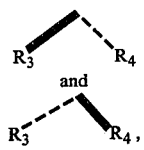

wherein $R_3$ and $R_4$ are hydrogen, methyl, or fluoro, being the same or different, with the proviso that one of $R_3$ and $R_4$ is fluoro only when the other is hydrogen or fluoro;

wherein g is one, 2, or 3; and wherein m is one to 5, inclusive.

2. A prostaglandin analog according to claim 1, wherein ⟩ is

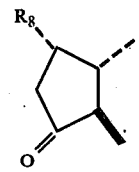

3. A prostaglandin analog according to claim 2, wherein $R_8$ is hydrogen.

4. A prostaglandin analog according to claim 2, wherein $R_8$ is hydroxy.

5. A prostaglandin analog according to claim 1, wherein ⟩ is

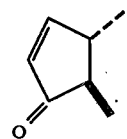

6. A prostaglandin analog according to claim 1, wherein ⟩ is

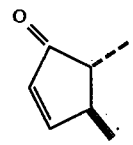

7. A prostaglandin analog according to claim 1, wherein ⟩ is

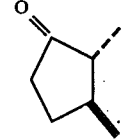

8. A prostaglandin analog according to claim 7, wherein $M_1$ is

9. 2-Decarboxy-2-hydroxymethyl-15-epi-3,7-inter-m-phenylene-3-oxa-4,5,6-trinor-13,14-didehydro-11-deoxy-PGE$_1$, a prostaglandin analog according to claim 8.

10. A prostaglandin analog according to claim 7, wherein M₁ is

11. A prostaglandin analog according to claim 10, wherein m is 3.
12. A prostaglandin analog according to claim 11, wherein g is 3.
13. 2-Decarboxy-2-hydroxymethyl-2a,2b-dihomo-3,7-inter-m-phenylene-4,5,6-trinor-3-oxa-15-methyl-13,14-didehydro-11-deoxy-PGE₁, a prostaglandin analog according to claim 12.
14. 2-Decarboxy-2-hydroxymethyl-2a,2b-dihomo-3,7-inter-m-phenylene-4,5,6-trinor-3-oxa-13,14-didehydro-11-deoxy-PGE₁, a prostaglandin analog according to claim 12.
15. A prostaglandin analog according to claim 11, wherein g is 1.
16. A prostaglandin analog according to claim 15, wherein at least one of R₃ and R₄ is methyl.
17. A prostaglandin analog according to claim 16, wherein R₃ and R₄ are both methyl.
18. 2-Decarboxy-2-hydroxymethyl-16,16-dimethyl-3,7-inter-m-phenylene-4,5,6-trinor-3-oxa-13,14-didehydro-11-deoxy-PGE₁, a prostaglandin analog according to claim 17.
19. A prostaglandin analog according to claim 15, wherein at least one of R₃ and R₄ is fluoro.
20. A prostaglandin analog according to claim 19, wherein R₃ and R₄ are both fluoro.
21. 2-Decarboxy-2-hydroxymethyl-3,7-inter-m-phenylene-4,5,6-trinor-3-oxa-16,16-difluoro-13,14-didehydro-11-deoxy-PGE₁, a prostaglandin analog according to claim 3.
22. A prostaglandin analog according to claim 15, wherein R₃ and R₄ are both hydrogen.
23. A prostaglandin analog according to claim 22, wherein R₅ is methyl.
24. 2-Decarboxy-2-hydroxymethyl-3,7-inter-m-phenylene-4,5,6-trinor-3-oxa-15-methyl-13,14-didehydro-11-deoxy-PGE₁, a prostaglandin analog according to claim 23.
25. A prostaglandin analog according to claim 22, wherein R₅ is hydrogen.
26. 2-Decarboxy-2-hydroxymethyl-3,7-inter-m-phenylene-4,5,6-trinor-3-oxa-13,14-didehydro-11-deoxy-PGE₁, a prostaglandin analog according to claim 25.
27. A prostaglandin analog according to claim 1, wherein D is

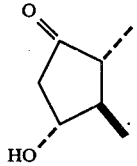

28. A prostaglandin analog according to claim 27, wherein M₁ is

29. A prostaglandin analog according to claim 28, wherein m is 3.
30. A prostaglandin analog according to claim 29, wherein g is 3.
31. 2-Decarboxy-2-hydroxymethyl-2a,2b-dihomo-3,7-inter-m-phenylene-4,5,6-trinor-3-oxa-15-epi-15-methyl-13,14-didehydro-PGE₁, a prostaglandin analog according to claim 30.
32. 2-Decarboxy-2-hydroxymethyl-2a,2b-dihomo-3,7-inter-m-phenylene-4,5,6-trinor-3-oxa-15-epi-13,14-didehydro-PGE₁, a prostaglandin analog according to claim 30.
33. A prostaglandin analog according to claim 29, wherein g is 1.
34. A prostaglandin analog according to claim 33, wherein at least one of R₃ and R₄ is methyl.
35. 2-Decarboxy-2-hydroxymethyl-15-epi-3,7-inter-m-phenylene-4,5,6-trinor-3-oxa-16,16-dimethyl-13,14-didehydro-PGE₁, a prostaglandin analog according to claim 34.
36. A prostaglandin analog according to claim 33, wherein at least one of R₃ and R₄ is fluoro.
37. 2-Decarboxy-2hydroxymethyl-3,7-inter-m-phenylene-4,5,6-trinor-3-oxa-15-epi-16,16-difluoro-13,14-didehydro-PGE₁, a prostaglandin analog according to claim 36.
38. A prostaglandin analog according to claim 33, wherein R₃ and R₄ are both hydrogen.
39. 2-Decarboxy-2-hydroxymethyl-3,7-inter-m-phenylene-4,5,6-trinor-3-oxa-15-epi-15-methyl-13,14-didehydro-PGE₁, a prostaglandin analog according to claim 38.
40. A prostaglandin analog according to claim 27, wherein M₁ is

41. A prostaglandin analog according to claim 40, wherein m is 3.
42. A prostaglandin analog according to claim 41, wherein g is 3.
43. A prostaglandin analog according to claim 42, wherein at least one of R₃ and R₄ is methyl.
44. 2-Decarboxy-2-hydroxymethyl-2a,2b-dihomo-3,7-inter-m-phenylene-4,5,6-trinor-3-oxa-16,16-dimethyl-13,14-didehydro-PGE₁, a prostaglandin analog according to claim 43.
45. A prostaglandin analog according to claim 42, wherein at least one of R₃ and R₄ is fluoro.
46. 2-Decarboxy-2-hydroxymethy-2a,2b-dihomo-3,7-inter-m-phenylene-4,5,6-trinor-3-oxa-16,16-difluoro-13,14-didehydro-PGE₁, a prostaglandin analog according to claim 45.
47. A prostaglandin analog according to claim 42, wherein R₃ and R₄ are both hydrogen.
48. 2-Decarboxy-2-hydroxymethyl-2a,2b-dihomo-3,7-inter-m-phenylene-4,5,6-trinor-3-oxa-15-methyl-13,14-didehydro-PGE₁, a prostaglandin analog according to claim 47.
49. A prostaglandin analog according to claim 41, wherein g is 1.
50. A prostaglandin analog according to claim 49, wherein at least one of R₃ and R₄ is methyl.
51. A prostaglandin analog according to claim 50, wherein only one of R₃ and R₄ is methyl.

52. 2-Decarboxy-2-hydroxymethyl-3,7-inter-m-phenylene-4,5,6-trinor-3-oxa-16-methyl-13,14-didehydro-PGE$_1$, a prostaglandin analog according to claim 51.

53. A prostaglandin analog according to claim 50, wherein R$_3$ and R$_4$ are both methyl.

54. 2-Decarboxy-2-hydroxymethyl-3,7-inter-m-phenylene-4,5,6-trinor-3-oxa-16,16-dimethyl-13,14-didehydro-PGE$_1$, a prostaglandin analog according to claim 53.

55. A prostaglandin analog according to claim 49, wherein at least one of R$_3$ and R$_4$ is fluoro.

56. A prostaglandin analog according to claim 55, wherein R$_3$ and R$_4$ are both fluoro.

57. A prostaglandin analog according to claim 56, wherein R$_5$ is methyl.

58. 2-Decarboxy-2-hydroxymethyl-3,7-inter-m-phenylene-4,5,6-trinor-3-oxa-15-methyl-16,16-difluoro-13,14-didehydro-PGE$_1$, a prostaglandin analog according to claim 57.

59. A prostaglandin analog according to claim 56, wherein R$_5$ is hydrogen.

60. 2-Decarboxy-2-hydroxymethyl-3,7-inter-m-phenylene-4,5,6-trinor-3-oxa-16,16-difluoro-13,14-didehydro-PGE$_1$, a prostaglandin analog according to claim 59.

61. A prostaglandin analog according to claim 49, wherein R$_3$ and R$_4$ are both hydrogen.

62. A prostaglandin analog according to claim 61, wherein R$_5$ is methyl.

63. 2-Decarboxy-2-hydroxymethyl-3,7-inter-m-phenylene-4,5,6-trinoro-3-oxa-15-methyl-13,14-didehydro-PGE$_1$, a prostaglandin analog according to claim 62.

64. A prostaglandin analog according to claim 61, wherein R$_5$ is hydrogen.

65. 2-Decarboxy-2-hydroxymethyl-3,7-inter-m-phenylene-4,5,6-trinor-3-oxa-13,14-didehydro-PGE$_1$, a prostaglandin analog according to claim 64.

* * * * *

UNITED STATES PATENT AND TRADEMARK OFFICE
CERTIFICATE OF CORRECTION

PATENT NO. : 4,134,921
DATED : January 16, 1979
INVENTOR(S) : Herman W. Smith

It is certified that error appears in the above-identified patent and that said Letters Patent are hereby corrected as shown below:

Column 3, lines 36-37, "according to claim 3" should read -- according to claim 20 --.

Signed and Sealed this

Twenty-ninth Day of May 1979

[SEAL]

Attest:

RUTH C. MASON
Attesting Officer

DONALD W. BANNER
Commissioner of Patents and Trademarks